US005637316A

United States Patent [19]
Ribier et al.

[11] Patent Number: 5,637,316

[45] Date of Patent: Jun. 10, 1997

[54] SLIMMING COMPOSITION FOR TOPICAL TREATMENT, CONTAINING TWO TYPES OF LIPOSOMES, AND USE THEREOF

[75] Inventors: Alain Ribier; Jean-Thierry Simonnet; Chantal Fanchon, all of Paris; Evelyne Segot, Nogent sur Marne; Herve Cantin, Savigny sur Orge, all of France

[73] Assignee: L'Oreal, Paris, France

[21] Appl. No.: 367,421

[22] Filed: Dec. 30, 1994

[30] Foreign Application Priority Data

Dec. 30, 1993 [FR] France .................................. 93 15866

[51] Int. Cl.⁶ .............................................. A61K 9/127
[52] U.S. Cl. ........................... 424/450; 424/401; 514/909
[58] Field of Search ............................... 424/450, 401; 514/909

[56] References Cited

U.S. PATENT DOCUMENTS 5,422,120  6/1995  Kim ........................................ 426/450

FOREIGN PATENT DOCUMENTS 0433131  6/1991  European Pat. Off. .
0559502  9/1993  European Pat. Off. .
2315991  1/1977  France .
2408387  6/1979  France .
2614787  11/1988  France .

OTHER PUBLICATIONS

International Journal Of Pharmaceutics, vol. 62, No. 1, Jul. 15, 1990, Elsevier NL, pp. 75–79, V. Gagrijelcic et al., "Evaluation of liposomes as drug carriers into the skin by one-dimensional epr imaging," p. 78, col. 2, table 2, p. 79, col. 1, paragraphs 2 and 3.

*Primary Examiner*—Gollamudi S. Kishore
*Attorney, Agent, or Firm*—Oblon, Spivak, McClelland, Maier & Neustadt, P.C.

[57] ABSTRACT

Compositions containing a first dispersion of lipid vesicles which are capable of penetrating into the deep layers of the skin and which contain at least one active agent chosen from lipolytic agents, draining agents and firming agents, for treating these deep layers, and a second dispersion of lipid vesicles which are capable of penetrating into the surface layers of the skin and which contain at least one active agent chosen from cutaneous surface treatment agents, exfoliation agents, smoothing agents and softening agents for the skin, for treating these surface layers, are effective as slimming agents for combating plumpness.

14 Claims, No Drawings

SLIMMING COMPOSITION FOR TOPICAL TREATMENT, CONTAINING TWO TYPES OF LIPOSOMES, AND USE THEREOF

BACKGROUND OF THE INVENTION

1. Field of the Invention

The present invention relates to compositions useful for decreasing and/or combating plumpness and/or excess weight for the purpose of obtaining a generalized or localized cosmetic and/or therapeutic slimming effect on the human or animal body. The present invention also relates to a method for slimming the body, by applying such a composition topically.

2. Discussion of the Background

Plumpness and/or excess weight is associated with the dysfunction of certain cells, known as adipocytes, which contain variable amounts of fats in the form of triglycerides which are themselves synthesized, in vivo by the adipocytes, enzymatically (lipogenesis) from free fatty acids and glucose contained in the body and supplied thereto via certain foods. In parallel with this, the triglycerides formed and then stored may be re-degraded, also via an enzymatic route (lipolysis), into fatty acids, glycerol and/or glycerol esters.

If, for various reasons, (poor hormonal functioning, excessively rich diet, inactivity, ageing), an appreciable imbalance develops in the body between lipogenesis and lipolysis in favor of lipogenesis, an accumulation of triglycerides occurs in the adipocytes, which may result in excess weight, possibly leading to obesity.

Although this excess weight was hitherto well tolerated, it nowadays constitutes, and especially in women, an ever-increasing problem both physical and aesthetic, or even psychological.

Several slimming methods have already been proposed for the purpose of combating excess weight, such as strict diets which as soon as they are stopped, very rapidly result in a new excess of weight which is often greater than that which was the cause of these diets, or alternatively surgical methods such as liposuction, these methods often being expensive and intricate.

The need thus exists for a "gentle" method, that is to say one which is not surgical or strict, for treating and/or preventing excess weight.

Many examples are known of cosmetic or dermatological compositions intended for treating the skin, which have one or more active agents that are suitable for treating the skin and which are encapsulated in lipid spherules or vesicles (also known as liposomes).

Lipid spherules or vesicles are understood to refer to particles formed of a membrane consisting of one or more concentric lamellae, these lamellae containing one or more bimolecular layers of amphiphilic lipids encapsulating an aqueous phase. The aqueous phase may contain water-soluble active substances and the bimolecular layers of amphiphilic lipids may contain lipophilic active substances.

These spherules generally have a mean diameter of between 10 nm and 5000 nm. Among the many documents published regarding this matter, there may be mentioned the French Certificate of Addition 2,408,387 which describes a composition based on aqueous dispersions of ionic or nonionic lipid spherules encapsulating at least one active substance. More precisely, this document describes compositions containing at least two dispersions of spherules containing different active agents, for the purpose of obtaining a mixed system, that is to say a system in which a first dispersion of spherules containing a first type of active substance is combined with a second dispersion of spherules containing another type of active substance, which enables the two types of substances to act simultaneously at the time of treatment and possibly to obtain a synergistic effect which would not be produced if these two types of substances were made to act successively and separately.

It is well known that the skin consists of surface layers, the stratum corneum, and of deep layers, the live epidermis and the dermis. However, specific delivery of such an active agent into the surface layers and, simultaneously, of the same or another active agent into the deep layers, is not known from the prior art.

Thus, there remains a need for a gentle method of combating plumpness. There also remains a need for compositions useful in such a method.

SUMMARY OF THE INVENTION

Accordingly, it is one object of the present invention to provide a novel method for combating plumpness.

It is another object of the present invention to provide a gentle method for combating plumpness.

It is another object of the present invention to provide novel compositions which are useful in such methods.

These and other objects which will become apparent during the following detailed description, have been achieved by the inventors' discovery that compositions comprising a first dispersion of lipid vesicles which are capable of penetrating into the deep layers of the skin and which contain at least one active agent chosen from lipolytic agents, draining agents and firming agents, for treating these deep layers, and a second dispersion of lipid vesicles which are capable of penetrating into the surface layers of the skin and which contain at least one active agent chosen from cutaneous surface treatment agents, exfoliation agents, smoothing agents and softening agents for the skin, for treating these surface layers, are effective slimming agents useful for combating plumpness and simultaneously treating the surface layers and deep layers of the skin.

The invention relates, therefore, to a slimming composition and to a cosmetic treatment process which fulfil this need. More particularly, this slimming composition comprises at least one active agent which is conveyed via at least two distinct types of lipid vesicles.

Thus, the inventors have now developed cosmetic slimming compositions, which allow the simultaneous action of two different active agents, and which furthermore allow these active agents to act in different areas of the skin, that is to say in the surface layers and in the deep layers of the skin, thereby very markedly enhancing the effectiveness of these compositions and the complementary or synergistic effect of the slimming active agents used.

The inventors have also developed cosmetic slimming compositions, which enable the same active agent to act simultaneously in the surface layers and in the deep layers of the skin, providing a more complete and therefore a more effective treatment against excess weight.

According to a specific embodiment, the active agents contained in the first dispersion of vesicles and in the second are the same.

DETAILED DESCRIPTION OF THE PREFERRED EMBODIMENTS

The Applicant has used a means of classifying vesicles which enables a person skilled in the art readily to select lipid vesicles capable of conveying the active agent to the deep layers of the skin, known as vesicles with deep-down action, and those capable of conveying the active agent to the surface layers of the skin, known as vesicles acting at the surface.

This classification is made on the basis of the diffusion constant D of a probe introduced into the vesicles. This probe is N-(1-oxyl-2,2,6,6-tetramethyl-4-piperidyl)-N,N-dimethyl-N-hydroxyethylammonium iodide, ASL, of formula (I):

$$\text{Me}-\text{N}^+-(\text{CH}_2)_2\text{OH, I}^- \quad (I)$$

[piperidinyl ring with N–O" substituent]

Vesicles for which the diffusion constant D of the probe into the stratum corneum is $>1\times10^{-7}$ cm$^2$ s$^{-1}$ are vesicles which are capable of penetrating into the deep layers of the skin.

Vesicles for which the diffusion constant D of the probe into the stratum corneum is $<1\times10^{-7}$ cm$^2$ s$^{-1}$ are vesicles which are capable of conveying the active agent to the surface layers of the skin.

The vesicles of the first type, the so-called vesicles with deep-down action, are generally in the fluid state at room temperature (about 20° C.), and those of the second type, the so-called vesicles acting at the surface, are generally in the gelled state at room temperature. The means of recognizing the state of the vesicles consists in determining the phase (fluid-gel lamellar) transition temperature of the main lipid constituting the membrane thereof, by differential thermal analysis (DTA).

Other characteristics of these vesicles relate to their ability to deliver the active agent to a greater or lesser depth in the skin. This is particularly the case for the degree of encapsulation.

Glucose is a labelling agent conventionally used for this type of determination (see in particular, Liposomes a practical approach by R.R.C. New, IRL Press, pp. 125–136 (1990)).

The degree of encapsulation is expressed as the volume of glucose solution encapsulated in the vesicles, measured in µl relative to the unit weight (mg) of the lipids constituting the membrane. This degree of encapsulation is determined immediately after the step of separation of the free glucose from the encapsulated glucose ($T_0$), as well as twenty-four hours after this separation ($T_{24\ hours}$).

The difference between these two successive determinations illustrates the permeability of the vesicles with respect to the encapsulated glucose, which may also be referred to as their encapsulation potential.

The first category of vesicles (delivering the active agent into the deep layers of the skin) has a high encapsulation potential for the small water-soluble molecules which are conventionally modelled by glucose, this encapsulation potential being maintained for at least 24 hours. The second category of vesicles (delivering the active agent into the surface layers of the skin) does not retain glucose in the encapsulated state for the same amount of time.

The main lipids constituting the vesicles of the first type (deep delivery of the active agent) are composed of at least one linear and saturated fatty chain of length ranging from 16 to 30 carbon atoms, such as hydrogenated phospholipids (from plants or from egg), saturated synthetic phospholipids such as dipalmitoylphosphatidylcholine, and polyol alkyl ethers or polyol alkyl esters containing one, two or three fatty chains per molecule. These lipids are used alone or as a mixture.

The main lipids constituting the vesicles of the second type (active agent delivered at the surface) are chosen in particular from the group comprising ionic lipids, especially such as natural plant- or egg-based phospholipids, containing unsaturated fatty chains having from 16 to 30 carbon atoms; nonionic lipids such as polyol alkyl ethers or polyol alkyl esters containing one or more fatty chains per molecule, including at least one fatty chain with a length of less than 16 carbon atoms, such as lauryl polyglyceryl-6-cetearyl glycol ether, described in detail in French Patent Application FR 92-09603 filed by L'Oréal, and mixtures thereof.

It is possible, in a known manner, to incorporate into the lipid phase constituting the lipid membrane of the vesicles, at least one additive chosen from the group formed of sterols (phytosterols, cholesterol or polyoxyethylenated phytosterols); long-chain alcohols, diols and triols (phytanetriol), long-chain amines and the quaternary ammonium derivatives thereof; phosphoric esters of fatty alcohols and the alkali metal (Na or K) salts thereof, such as dicetyl phosphate, sodium dicetyl phosphate, alkyl sulfates (sodium cetyl sulfate), alkali metal salts of cholesterol sulfate or of cholesterol phosphate, the sodium salt of phosphatidic acid, and lipoamino acids and the salts thereof, such as the sodium acylglutamates.

Examples of vesicles of the first type (delivering the active agent into the deep layers of the skin) which may be mentioned are vesicles obtained from the following lipids (CTFA name):

A/cholesterol/casein lipoamino acid, especially in a 45/45/10 weight ratio (where A is a triglyceryl cetyl ether marketed by the company Chimex under the name Chimexane NL);

B/cholesterol/dicetyl phosphate, especially in a 60/35/5 weight ratio (where B is a mixture of triglyceryl mono-, di- and tricetyl ether, marketed by the company Chimex under the name Chimexane NT);

Span 40 (from ICI, or Sorbitan palmitate)/cholesterol/sodium acylglutamate (sold under the name HS11 by the company Ajinomoto), especially in a 47.5/47.5/5 weight ratio;

PEG 8 stearate/cholesterol/sodium acylglutamate, especially with a 47.5/47.5/5 weight ratio (where PEG 8 stearate is polyethylene glycol containing 8 units of ethylene oxide, marketed by the company Unichema under the name PEG 400 stearate);

PEG 8 stearate/cholesterol/phytanetriol/sodium acylglutamate, especially with a 47.5/20/27.5/5 weight ratio;

Hydrogenated lecithin/polyoxyethylenated phytosterol containing 5 units of ethylene oxide, especially in a 60/40 weight ratio;

Polyoxyethylenated methylglucose distearate containing 20 units of ethylene oxide/cholesterol/sodium acylglutamate, especially in a 45/45/10 weight ratio (the distearate being, for example, that sold under the name Glucam E 20 distearate by Amerchol);

A/cholesterol/dicetyl phosphate, especially with a 47.5/47.5/5 weight ratio;

Diglyceryl distearate (for example that sold by Nihon under the name Emalex DS G2)/cholesterol/sodium acylglutamate, in a 45/45/10 weight ratio;

Sucrose mono- and distearate (for example that sold by Grillo under the name Grilloten PSE 141 G)/cholesterol/sodium acylglutamate, especially in a 45/45/10 weight ratio;

Tetraglyceryl tristearate (for example that sold by Nikkol under the name Tetraglyn 3S)/cholesterol/sodium acylglutamate, especially in a 45/45/10 weight ratio.

Examples of vesicles of the second type (delivering the active agent into the surface layers of the skin) which may be mentioned are vesicles obtained from the following lipids:

Sunflower lecithin;

Natipide II (soya lecithin/ethanol/water in a 20/16/64 weight ratio, marketed by Nattermann);

C (soya lecithin/cholesterol/propylene glycol in a 60/20/20 weight ratio, marketed by Nattermann under the name NAT 50 PG);

D/dimyristyl phosphate, especially in a 95/5 weight ratio (where D is a lauryl polyglyceryl-6-cetearyl glycol ether marketed by the company Chimex under the name Chimexane NS).

Table I below gives, for some of the vesicles obtained using the above lipids, the diffusion constant D for ASL in the stratum corneum and in the epidermis/dermis, as well as the degree of encapsulation of glucose and the phase transition temperature of the main lipid constituting the membrane. The diffusion constant was measured for an encapsulated ASL concentration of 0.35% by weight based on the total weight of the composition.

Measurement of the diffusion constant D is carried out by combining two methods using a paramagnetic probe, ASL: one-dimensional and periodic electron paramagnetic resonance (EPR), on the one hand, and EPR kinetic imaging, on the other hand. These two methods are respectively described in the articles "Evaluation of liposomes as drug carriers into the skin by one-dimensional EPR imaging" by V. Gabrijelcic et al., *International Journal of Pharmaceutics*, vol. 62, pp. 75–79, Elsevier (1990), and "Liposome entrapped molecules penetration into the skin measured by nitroxide reduction kinetic imaging" by V. Gabrijelcic et al., *Periodicum Biologorum*, vol. 93, No. 2, pp. 245–246 (1991).

Measurement of the degree of encapsulation is carried out as described in the Liposomes a practical approach, by R.R.C. New, IRL Press, pp. 125–136 (1990) cited above, and that of the phase transition temperature is carried out as described above.

Advantageously, several active agents are used simultaneously in each category of vesicles, these active agents having the same function and/or imparting to the skin, at the surface and deep down, the same type of effect; the agents active at the surface and the agents with deep-down action are thus complementary.

The agents active at the surface and the active agents with deep-down action which may be used in the invention are those that are conventionally used in the cosmetic and/or dermatological field. They may be present in an amount of from 0.02 to 10% by weight, preferably 0.1 to 5% by weight, based on the total weight of the composition.

The active agents with deep-down action are, for example, chosen from asiatic acid; caffeine; nicotinic acid

TABLE I

| Ref. | LIPID SYSTEMS | Proportions % by weight (mg) | Diffusion coefficient D in $10^{-7}$ cm$^2$ s$^{-1}$ in the stratum corneum | Diffusion coefficient D in $10^{-7}$ cm$^2$ s$^{-1}$ in the epidermis/ dermis | Degree of encapsulation of glucose in μl/mg $T_o$ | Degree of encapsulation of glucose in μl/mg $T_{24\,h}$ | Phase transition temperature in °C. |
|---|---|---|---|---|---|---|---|
| | 1st type - deep down | | | | | | |
| 1 | A/cholesterol/casein lipoamino acid | 45/45/10 (67.5/67.5/15) | 42 | 5 | 7.5 | 6.8 | 50 |
| 2 | B/cholesterol/dicetyl phosphate | 60/35/5 (90/52.5/7.5) | 58 | 2 | 11.1 | 11.1 | 54 |
| 3 | Span 40/cholesterol/ sodium acylglutamate | 47.5/47.5/5 (71.25/71.25/7.5) | 42 | 2 | 13.8 | 13.8 | 50 |
| 4 | PEG 8 stearate/ cholesterol/sodium acylglutamate | 47.5/47.5/5 (71.25/71.25/7.5) | 42 | 2 | 14.4 | 14.4 | 55 |
| 5 | PEG 8 stearate/ cholesterol/phytanetriol/ sodium acylglutamate | 47.5/20/27.5/5 (71.25/30/41.25/7.5) | 8.3 | 2.5 | 4.1 | 3.0 | 55 |
| 6 | Hydrogenated lecithin/ polyoxyethylenated phytosterol | 60/40 (90/60) | 8 | 2 | 6.0 | 4.8 | 80 |
| | 2nd type - surface | | | | | | |
| 7 | Sunflower lecithin | 100 (150) | 0.3 | 0.2 | 1.6 | 0 | <0 |
| 8 | Natipide II (soya lecithin/ethanol/water) | 20/16/64 (30/24/96) | 0.4 | 0.2 | 0.4 | 0 | <0 |
| 9 | C (soya lecithin/ sterols/propylene glycol) | 60/20/20 (90/30/30) | 0.25 | 0.1 | 1.8 | 0 | <0 |
| 10 | D/dimyristyl phosphate | 95/5 (142.5/7.5) | 0.3 | 0.2 | 2.0 | 0 | 14 | derivatives, such as α-tocopherol nicotinate or hexyl nicotinate; silicon; carnitine; coenzyme Q; escin; ruscogenin; draining, firming, lipolytic or veinotropic plant extracts; anti-glucose-uptake active agents; α-2-blocker compounds capable of blocking the α-2 receptors at the surface of adipocytes, such as ginkgo biloba.

As plant extracts which may be used in the invention, there may in particular be mentioned ivy, seaweed, butcher's broom, common horse chestnut, arborvitae, arnica, wild pansy, clematis, cola, blackcurrant, tea and rosemary.

The agents active at the surface are chosen, for example, from keratolytic agents, such as 5-octanoylsalicylic acid; salicylic acid; α-hydroxy acids such as lactic acid, malic acid, glycolic acid or tartaric acid or α-hydroxy acids from fruit, such as citric acid; and moisturizing agents.

As moisturizing agents which may be used in the invention, there may be mentioned polyhydroxylated alcohols such as sorbitol, glycerine, hexanetriol, propylene glycol, hexylene glycol and polyethylene glycols; sugars and the derivatives thereof; starches and the derivatives thereof; D-panthenol; hyaluronic acid; monoethanolamine lactamide and monoethanolamine acetamide; 2-pyrrolidone-5-carboxylic acid; as well as mixtures of these various active agents.

The compositions according to the invention may be provided in all the pharmaceutical forms normally used for topical application, such as aqueous gels, emulsions, lotions, ointments, sera and, more particularly, vesicle-dispersed oil droplets such as those described in French patents FR-A-2,485,921 and FR-A-2,490,504.

As is known, in addition to the vesicles, a vegetable oil, mineral oil, silicone-containing oil or synthetic oil which is dispersed in an aqueous phase, and also hydrophilic adjuvants such as gelling agents, antioxidants, preserving agents, opacifying agents, lipophilic adjuvants such as essential oils and fragrances, pigments and fillers, may be found in the compositions of the invention, as described in the above French patents. For example, polyethylene beads may be added to provide a cleaning action (scrub). The dispersed oil may be present in an amount of from 2 to 40% by weight, preferably 5 to 20% by weight, based on the total weight of the composition, and the adjuvants may be present in a total amount of from 0.1 to 10% by weight, preferably 1 to 5% by weight, based on the total weight of the composition.

The invention also relates to a use of the composition defined above and to a process for decreasing and/or combating plumpness and/or excess weight on the human body, involving applying this composition locally or over all of the skin of the body. The invention also relates to a use of this composition for the preparation of an ointment intended to decrease and/or to combat plumpness and/or excess weight.

The vesicles of both the first and second types suitably comprise 1 to 90% by weight, preferably 5 to 70% by weight, more preferably 5 to 20% by weight, of the total weight of the composition.

The relative amounts of the vesicles of the first and second types in the present compositions are suitably:

10 to 90% by weight of the vesicles of the first type, and 90 to 10% by weight of the vesicles of the second type, preferably:

30 to 70% by weight of the vesicles of the first type, and 70 to 30% by weight of the vesicles of the second type, based on the total weight of the vesicles of the first and second types.

Other features of the invention will become apparent in the course of the following description of exemplary embodiments which are given for illustration of the invention and are not intended to be limiting thereof.

EXAMPLES

In all of the Examples, the term "qs 100 g" means that that ingredient is added in a sufficient amount so that the sum of the amounts of all of the ingredients is 100 g.

A. Production of lipid vesicles containing ASL

The constituent lipids of the wall of the vesicles are weighed and dissolved in 10 ml of methanol. The alcoholic solution is then transferred into a 50-ml round-bottomed flask with a ground joint, which is subsequently placed on a rotary evaporator such that the contents are thermostatted at a temperature of 30° C. The evaporation is continued until a dry film of lipids is deposited on the wall of the flask.

3 ml of an aqueous 0.01 molar solution of ASL are then added to the flask, which is subsequently shaken by hand for about 10 minute, either at room temperature (20° C.) for the vesicles of Table I of reference Nos. 7 to 10, or at a temperature of 50° C. for the vesicles of reference Nos. 1 to 6 of Table I. The medium is then left to equilibrate at room temperature for 2 hours, after which the dispersion is placed in a dialysis bag and in contact with 500 ml of distilled water. Dialysis takes place overnight. The next day, the water is changed and the dialysis is continued for a further 4 hours.

A cotton thread 0.3 mm thick is then soaked in the vesicle dispersion and then placed in contact with a section of skin cut from a pig's ear which has been freshly taken from an abattoir intended for food supply.

The ear sample taken is rinsed with water and cut into slices 1 mm thick, 5 mm wide and 10 mm long and then placed in a maintenance cell. Measurements of the diffusion of ASL into the skin are made in the 24 hours following the taking of the skin sample.

B. Production of the cosmetic composition

1. Production of vesicles of the first type (diffusing deep down)

The vesicles (with deep-down action) are prepared membrane constituent having the lowest melting point $T_m$ is according to a common method for co-fusion of the various membrane constituents chosen (see Table I). Thus, the membrane constituent having the lowest melting point $T_m$ is melted. The other membrane constituents are added, and the mixture is then homogenized with moderate stirring and is finally partially hydrated, while maintaining the melting temperature $T_m$ defined above.

An aqueous solution of at least one first active agent for the deep-down treatment is added to the paste obtained. The mixture is stirred with a turbine for 1 hour and 30 minutes in order to hydrate fully, while maintaining the temperature $T_m$. One or more other active agents for the deep-down treatment are added to the reaction medium, homogenization is carried out and the temperature of the medium is lowered to room temperature (20° C.).

2. Production of vesicles of the second type (diffusing at the surface)

An aqueous solution of one (or more) second active agent for the surface treatment is introduced, at room temperature (20° C.) and with simple stirring, into the chosen mixture of constituents which are to form the membrane of the vesicles acting at the surface (see Table I). Vesicles acting at the surface encapsulating the second active agent acting at the surface are thus obtained.

3. production of the "double-liposome" composition

The fatty phase (the oils) of the composition is added to the medium containing the vesicles with deep-down action, and it is dispersed (at room temperature) with stirring. The reaction medium obtained is then mixed with that containing the vesicles acting at the surface. The adjuvants, such as preserving agents, a gelling agent which may be neutralized if necessary with a base (triethanolamine or sodium hydroxide), and fragrances, etc., are then optionally added.

The product obtained is in the form of a soft and smooth white cream which may be used in the cosmetic and/or dermatological field for treating plumpness and/or excess weight on the human and possibly animal body.

Specific examples of cosmetic compositions in accordance with the invention are given below.

Example 1

Double-liposome slimming cream

| Preparation A: Liposomes with deep-down action: | |
| --- | --- |
| Triglyceryl cetyl ether | 7.6 g |
| Cholesterol | 7.6 g |
| Sodium acylglutamate | 0.8 g |
| Asiatic acid (active agent) | 0.2 g |
| Nipagine (preserving agent) | 0.1 g |
| Demineralized water | qs 100 g |
| Preparation B: Liposomes active at the surface: | |
| Chimexane NS/dimyristyl phosphate in a 95/5 weight ratio | 20.0 g |
| Salicylic acid (active agent) | 2.0 g |
| Glycerine (active agent) | 15.0 g |
| Nipagine (preserving agent) | 0.2 g |
| Demineralized water | qs 100 g |
| Double-liposome composition: | |
| Preparation A | 12.5 g |
| Preparation B | 10.0 g |
| Oils (vegetable oils and silicone oils) | 8.6 g |
| Plant extracts | 4.1 g |
| Preserving agents | 0.7 g |
| Carboxyvinyl polymer (gelling agent) | 0.9 g |
| Sodium hydroxide | 1.8 g |
| Demineralized water | qs 100 g |

The cream obtained may be applied daily either locally or all over the body in order to decrease, or even to eliminate, excess weight.

Example 2

Double-liposome slimming cream

This cream differs from that of Example 1 in that 5-n-octanoylsalicylic acid is used as the agent active at the surface, instead of salicylic acid.

Example 3

Double-liposome slimming cream

| Preparation A: Liposomes with deep-down action: | |
| --- | --- |
| PEG 8 stearate | 7.6 g |
| Cholesterol | 7.6 g |
| Sodium acylglutamate | 0.8 g |
| Caffeine (active agent) | 3.0 g |
| 98% Triethanolamine (neutralizing agent) | 1.5 g |
| Salicylic acid | 1.3 g |
| Methylparaben (preserving agent) | 0.1 g |
| Demineralized water | qs 100 g |

| -continued | |
| --- | --- |
| Preparation B: Liposomes active at the surface: | |
| Chimexane NS | 20.0 g |
| Glycerine (active agent) | 15.0 g |
| 5-n-Octanoylsalicylic acid (active agent) | 2.0 g |
| Methylparaben (preserving agent) | 0.2 g |
| Demineralized water | qs 100 g |
| Double-liposome composition: | |
| Preparation A | 12.5 g |
| Preparation B | 10.6 g |
| Oils (vegetable oils and silicone oils) | 8.6 g |
| Carboxyvinyl polymer (gelling agent) | 0.9 g |
| Sodium hydroxide | 1.8 g |
| Preserving agents | 0.5 g |
| Demineralized water | qs 100 g |

This application is based on French Patent Application 93-15866 filed on Dec. 30, 1993, which is incorporated herein by reference in its entirety.

Obviously, numerous modifications and variations of the present invention are possible in light of the above teachings. It is therefore to be understood that, within the scope of the appended claims, the invention may be practiced otherwise than as specifically described herein.

What is claimed as new and is desired to be secured by Letters Patent of the United States is:

1. A composition for the simultaneous treatment of the layers of the stratum corneum and deep layers of the skin, comprising:

(a) a first dispersion of lipid vesicles which are capable of penetrating into said deep layers of the skin and which contain at least one active agent selected from the group consisting of lipolytic agents, draining agents and firming agents, for treating said deep layers; and (b) a second dispersion of lipid vesicles which are capable of penetrating into said layers of the stratum corneum of the skin and which contain at least one active agent selected from the group consisting of cutaneous surface treatment agents, exfoliation agents, smoothing agents and softening agents for the skin, for treating said layers of the stratum corneum, and wherein said vesicles of said first dispersion ensure a distribution of N-(1-oxyl-2,2,6,6-tetramethyl-4-piperidyl)-N-dimethyl-N-hydroxyethylammonium iodide (ASL) in the stratum corneum $>1\times10^{-7}$ cm$^2$/s and in that said vesicles of said second dispersion ensure a distribution of ASL in the stratum corneum $<1\times10^{-7}$ cm$^2$/s.

2. The composition of claim 1, wherein said vesicles of said first dispersion are in a fluid state at room temperature and said vesicles of said second dispersion are in a gelled state at room temperature.

3. The composition of claim 1, wherein said vesicles of said first dispersion exhibit an encapsulation potential of glucose for at least 24 hours, and said vesicles of said second dispersion exhibit an encapsulation potential of glucose for less than 24 hours.

4. The composition of claim 1, wherein said vesicles of said first dispersion are formed of lipids having at least one linear and saturated fatty chain having from 16 to 30 carbon atoms.

5. The composition of claim 1, wherein said vesicles of said first dispersion are formed of at least one lipid selected from the group consisting of natural hydrogenated phospholipids, saturated synthetic phospholipids, polyol alkyl ethers having at least one linear fatty chain, polyol alkyl esters having at least one fatty chain, and mixtures thereof.

6. The composition of claim 1, wherein said vesicles of said first dispersion are formed of lipids selected from the group consisting of:

triglyceryl cetyl ether, cholesterol, and casein lipoamino acid; mixtures of triglyceryl mono-, di- and tricetyl ether, cholesterol, and dicetyl phosphate; triglyceryl cetyl ether, cholesterol, and dicetyl phosphate; sorbitan palmitate, cholesterol, and sodium acylglutamate; PEG 8 stearate, cholesterol, and sodium acylglutamate; diglyceryl distearate, cholesterol, and sodium acylglutamate; sucrose mono- and distearate, cholesterol, and sodium acylglutamate; PEG 8 stearate, cholesterol, phytanetriol, and sodium acylglutamate; polyoxyethylenated methylglucose distearate containing 20 mol of ethylene oxide, cholesterol, and sodium acylglutamate; hydrogenated lecithin, and polyoxyethylenated phytosterol; and tetraglyceryl tristearate, cholesterol, and sodium acylglutamate.

7. The composition of claim 1, wherein said vesicles of said second dispersion are formed of lipids selected from the group consisting of natural ionic phospholipids having unsaturated fatty chains having from 16 to 30 carbon atoms, polyol alkyl ethers having at least one fatty chain per molecule, comprising at least one fatty chain with a length of less than 16 carbon atoms, polyol alkyl esters having at least one fatty chain per molecule, comprising at least one fatty chain with a length of less than 16 carbon atoms.

8. The composition of claim 1 wherein said vesicles of said second dispersion are formed of at least one lipid selected from the group consisting of: sunflower lecithin; soya lecithin, ethanol, and water; soya lecithin, cholesterol, and propylene glycol; and lauryl polyglyceryl-6-cetearyl glycol ether and dimyristyl phosphate.

9. The composition of claim 1, wherein said active agent of said first dispersion and said active agent of said second dispersion provide the same function, the same effect or both.

10. The composition of claim 1, wherein said active agent of said first dispersion and said active agent of said second dispersion are the same.

11. The composition of claim 1, wherein said active agent contained in said first dispersion is selected from the group consisting of asiatic acid; caffeine; nicotinates; silicon; carnitine; coenzyme Q; escin; ruscogenin; plant extracts, anti-glucose-uptake active agents, and $\alpha$-2-blocker compounds.

12. The composition of claim 1, wherein said active agent contained in said second dispersion is selected from the group consisting of 5-octanoylsalicylic acid, salicylic acid, $\alpha$-hydroxy acids, and moisturizing agents.

13. The composition of claim 1, further comprising (c) an oily phase dispersed in an aqueous phase.

14. The composition of claim 1, further comprising (d) a hydrophilic or lipophilic adjuvant.

* * * * *